US009056089B2

(12) United States Patent
Delarcina, Jr. et al.

(10) Patent No.: US 9,056,089 B2
(45) Date of Patent: Jun. 16, 2015

(54) PROCESS OF PREPARING JAMBU EXTRACT, USE OF SAID EXTRACT, COSMETIC COMPOSITIONS COMPRISING THEREOF AND COSMETIC PRODUCTS COMPRISING SAID COSMETIC COMPOSITIONS

(75) Inventors: Sergio Delarcina, Jr., São Paulo (BR); José Renato Cagnon, Jundiaí (BR); Alexandre Roberto Silva, Jundiaí (BR); Viviane Emi Nakano Fukusawa, São Paulo (BR)

(73) Assignee: Natura Cosmeticos S.A., Sao Paulo (BR)

(*) Notice: Subject to any disclaimer, the term of this patent is extended or adjusted under 35 U.S.C. 154(b) by 516 days.

(21) Appl. No.: 11/908,621

(22) PCT Filed: Mar. 21, 2006

(86) PCT No.: PCT/BR2006/000056
§ 371 (c)(1),
(2), (4) Date: Mar. 6, 2008

(87) PCT Pub. No.: WO2006/099707
PCT Pub. Date: Sep. 28, 2006

(65) Prior Publication Data
US 2008/0171003 A1      Jul. 17, 2008

(30) Foreign Application Priority Data
Mar. 23, 2005   (BR) ........................................ 500886

(51) Int. Cl.
*A61K 36/28* (2006.01)
*A61K 8/97* (2006.01)
*A61Q 19/00* (2006.01)

(52) U.S. Cl.
CPC . *A61K 36/28* (2013.01); *A61K 8/97* (2013.01); *A61Q 19/00* (2013.01)

(58) Field of Classification Search
CPC ............ A61K 8/42; A61K 8/922; A61K 8/97
See application file for complete search history.

(56) References Cited

U.S. PATENT DOCUMENTS 2,713,584 A * 7/1955 Gisvold ........................ 540/145
3,720,762 A * 3/1973 Hatasa et al. .................. 424/58
5,194,583 A * 3/1993 Krulik ........................... 528/485

FOREIGN PATENT DOCUMENTS

| EP | 1 352 640 | 10/2003 | |
|---|---|---|---|
| EP | 1352640 | * 10/2003 | ............... A61K 7/48 |
| GB | 740 630 | 11/1955 | |

OTHER PUBLICATIONS

Zubrick, James W.; "The Organic Chem Lab Survival Manual: A Student's Guide to Techniques 4th ed.," 1997; John Wiley & Sons Inc.; pp. 1-26.*
Ramsewak, Russel S.; Erikson, Andrew J.; Nair, Muraleedharan G.; "Bioactive N-isobutylamides from the flower buds of *Spilanthes acemella*," 1999, PERGAMON, Phytochemistry, vol. 51, pp. 729-732.*
Burdock, George A.; "Fenaroli's Hanbook of Flavor Ingredients 5th edition," 2004; CRC Press; entry for "Jambu Oleoresin," pp. 1-6.*
Lewis, Richard J., Sr.; "Hawley's Condensed Chemical Dictionary, 14th Edition," 2002; John Wiley & Sons; entry for "aluminum sulfate," pp. 1-2.*
O'Neil, Maryadele J.; Heckelman, Patricia E.; Koch, Cherie B.; Roman, Kristin J.; Kenny Catherine, M.; D'Arecca, Maryann R. editors; "The Merck Index: An Encyclopedia of Chemicals, Drugs, and Biologicals," 2006; Merck & Co., Inc.; entries for "affinin" and "aluminum sulfate," pp. 1-11.*
Zubrick, James W.; "The Organic Chem Lab Survival Manual: A Student's Guide to Techniques 4th ed.," 1997; John Wiley & Sons Inc.; pp. 1-26.*
Ramsewak, Russel S.; Erikson, Andrew J. Nair, Muraleedharan G.; "Bioactive N-isobutylamides from the flower buds of *Spilanthes acemella*," 1999, Pergamon, Phytochemistry, vol. 51, pp. 729-732.*
Technical Report No. IN0001/05; *Contraction of Collagen Gel and a Skin Permeation Study* (Translation Included).
Dr. Jean Luc Gesztesi; Final Report of the Study RS041101P;*Biological Activity of Compounds on the Contraction Frequency of Muscle Cells Cocultured with Spinal Cord Explant*;Feb. 3, 2005; BIOalternatives Societe Anonyme, France.
The International Search Report for PCT Application No. PCT//BR2006/000056; Filed Mar. 21, 2006; Date of Completion Jul. 25, 2006; Date of Mailing Aug. 3, 2006.
The Written Opinion for PCT Application No. PCT//BR2006/000056; Filed Mar. 21, 2006; Date of Completion Jul. 25, 2006; Date of Mailing Aug. 3, 2006.
The Response to Written Opinion Dated Jan. 23, 2007.
The International Preliminary Report on Patentability for PCT Application No. PCT/BR2006/000056; Filed Mar. 21, 2006; Date of Submission of Demand Jan. 23, 2007; Date of Completion of Report Jun. 11, 2007.

* cited by examiner

*Primary Examiner* — David J Blanchard
*Assistant Examiner* — Ivan Greene
(74) *Attorney, Agent, or Firm* — Alston & Bird LLP

(57) ABSTRACT

The present invention discloses a process of preparing jambu extract that results in a jambu extract free from chlorophyll and derivatives of this compound. It is a method for isolating the components of interest in a simplified way, with quite high process yield, higher than 85%. The present invention further relates to the use of this extract in preparing cosmetic compositions, the cosmetic compositions comprising said extract, and to cosmetic products comprising said cosmetic compositions.

6 Claims, 1 Drawing Sheet

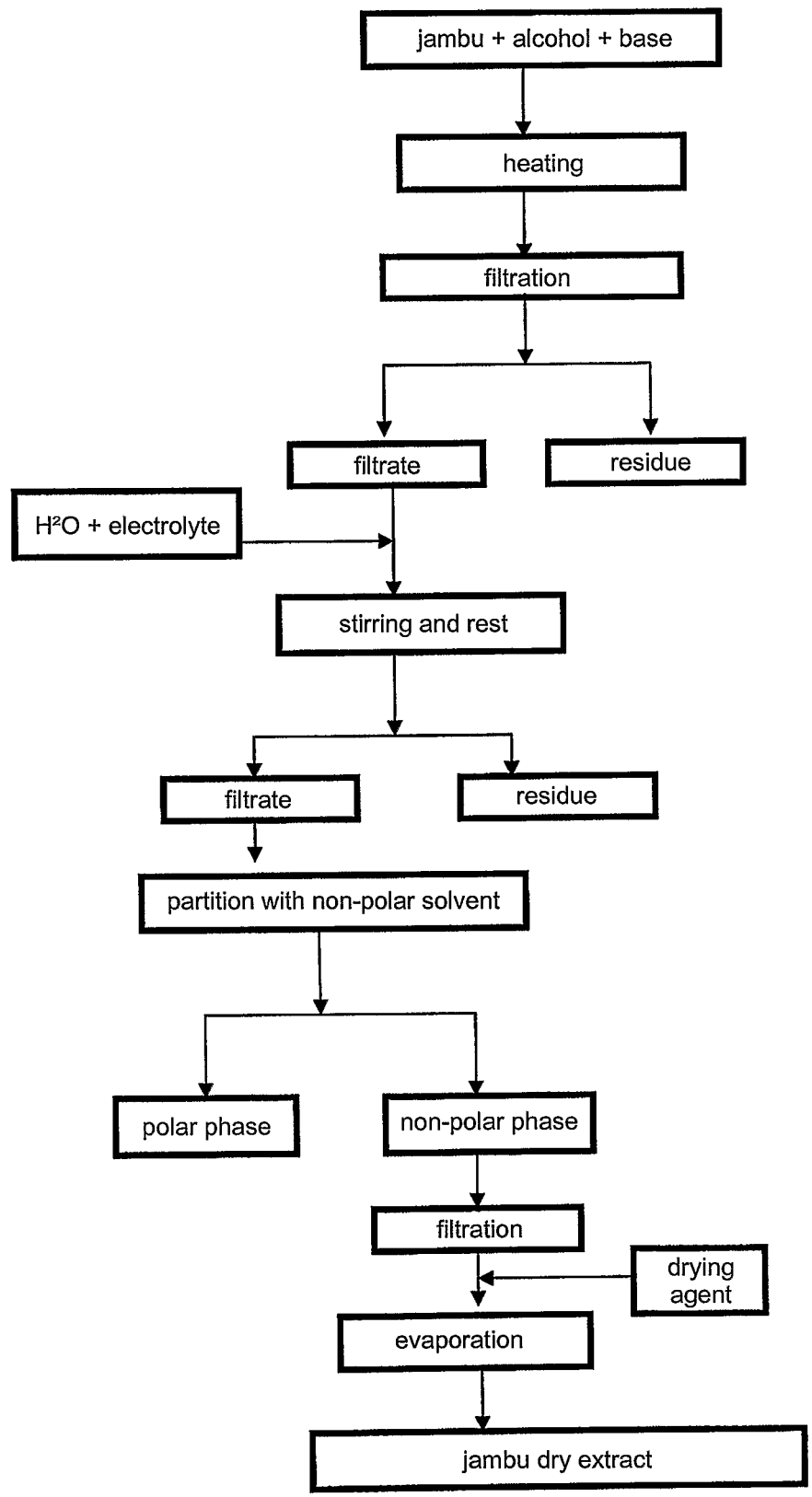

PROCESS OF PREPARING JAMBU EXTRACT, USE OF SAID EXTRACT, COSMETIC COMPOSITIONS COMPRISING THEREOF AND COSMETIC PRODUCTS COMPRISING SAID COSMETIC COMPOSITIONS

FIELD OF THE INVENTION

The present invention relates to a process of preparing a jambu extract free from chlorophyll and derivatives of this compound. This is a method for isolating the components of interest in a simplified way, by means of selective basic hydrolysis of chlorophyll. The present invention further relates to the use of this extract in the preparation of cosmetic compositions, to cosmetic compositions comprising said extract standardized in spilanthol contents [CAS 25394-57-4] of about 20.30% to 28.7%, and to cosmetic products comprising said cosmetic compositions, with final spilanthol content ranging from 0.001% to 10.00%.

DESCRIPTION OF THE PRIOR ART

Jambu (*Spilanthes oleracea* or *Spilanthes acmella* var *oleracea* or *Acmella oleracea*) is an annual plant of the family Compositae originating in South America. In the Brazilian state of Para it is a fundamental part of the traditional cooking, taking part in typical dishes such as "tacacá" and "pato no tucupi".

The inflorescences, composed of yellow flowers, and the leaves have a pungent flavor and so they are used in cooking or in popular medicine, mainly as analgesic for toothache. Its properties are attributed mainly to the spilanthol [CAS 25394-57-4], which is an isobutylamide having the following formula:

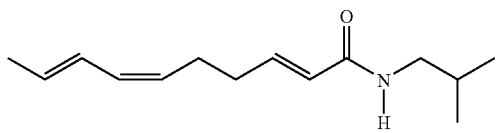 [SMILES: C/C=C/C=C\CC/C=C/C(=O)NCC(C)C]

This chemical compound is quite known for having several chemical-pharmaceutical applications, besides the use in cooking, as already said.

It is used, for instance:
as an analgesic for toothache;
for the treatment of aphtha and herpes;
for stomatitis and infections in the throat;
as a sialagogue;
as a cicatrizant.

Other biological and pharmacological activities are also known, namely:
as a larvicide against larvae of *Culex quinquefasciatus*;
as an antimicrobial agent against *Proteus mirabilis, Pseudomonas aeruginosa, Staphylococcus aureus* and *Candida albicans*;
as a fungistat and fungicide against *Aspergillus* spp;
an antimutagenic agent;
as an insecticide effective against *Aedes aegyptii*, tick, cockroaches and clothes moths.

In addition to spilanthol, jambu comprises the terpenoids: limonene, β-caryophyllene, (Z)-β-ocimene, germacrene-B, germacrene-D, mircene, α-humalene, among other chemical compounds.

Some applications of spilanthol in the area of cosmetics are already known from the prior art, the main ones being cited below:

Document US 20020012640 discloses a cosmetic composition for stressed skin under extreme conditions, which comprises treatment portions for various types of climate. The treatment portion for hot climate contains a botanical ingredient to provide a feeling of cold or to induce a feeling of softness, improving the effects caused by high temperatures. One of the compounds cited for performing this function is a spilanthol derivative (menthone glycerol ketal spilanthol).

Document PI 0100254-6 describes compositions recommended, among other functions, for personal care as cosmetics, which comprise at least a component that provides a refreshing feeling, a component that provides a feeling of warming up and a third component that provides a tingling sensation. The components indicated for acting in this last function are jambu oil-resin and spilanthol.

Document PI 0204271-1 discloses antidandruff compositions and antipruritic compositions present in products intended for personal care such as shampoos, creams, among others, which comprise an antidandruff agent and refreshing components such as jambu oil-resin and spilanthol.

Further, document JP 6072858 relates to detergent composition for the body, which comprises spilanthol, preferably from 0.005% to 2.000% by weight of spilanthol. This composition acts on the body in a soft manner, provides a moderate stimulus to the skin and a refreshing and calming sensation.

Document JP 60215610 discloses a preparation for bath, which contains spilanthol from *Spilanthes acmella*. This preparation provides a sedative and adstringent action to the skin, besides providing relief from muscular pains.

Finally, document JP 51032741 describes the use of spilanthol extracted from plants in cosmetic bases. This base provides a prolonged refreshing sensation.

On the other hand, so far one does not know techniques or processes for isolating spilanthol or for preparing jambu extract in the absence of chlorophyll. Further, in most of the above-cited compositions synthetic spilanthol is used.

Some processes are known from the prior art for removing chlorophyll from oils or plant extracts. With this removal, one achieves an increase in the commercial value of the extract, mainly because one removes the dark-green coloration, thus bringing about colorless cosmetic formulations or formulations with other colorations than greenish, improving the aspect and raising the commercial appeal.

However, the known processes employed several steps and expensive reactants. Besides, there is not yet a process designed for obtaining extract from jambu, the jambu extract being free from chlorophyll, a product still little exploited.

Anyway, the applicant lists below documents that deal with the removal of chlorophyll from plant oils, although none of them relates to jambu proper.

Document U.S. Pat. No. 4,781,864 discloses a process of removing chlorophyll, colored bodies and phospholipids from glyceride oils, by contacting said oil with silica adsorbents treated with acid provided with an amorphous silica surface. These oils may be either edible oils from fruits and plants or non-edible oils from petroleum.

Document GB 740630 describes a process of obtaining chlorophyll by saponification of chlorophyll, extraction of chlorophyll and its derivatives by using specific solvents and treatment with acid for purifying the chlorophyll and its derivatives.

On the other hand, document U.S. Pat. No. 4,049,520 discloses a process for improving the color of organic liquids such as fats and plant oils, which contain impurities such as chlorophyll. Said liquid is subjected to refining steps using the aqueous reactant and hydrogenation reaction. The organic liquid is mixed with solid particles of absorbent material in order to remove the colored bodies.

Another process for removing chlorophyll is described in document U.S. Pat. No. 5,315,021. In this process, one used phosphoric acid in order to bring about the precipitation of chlorophyll and its derivatives and then uses bleaching clay.

Document U.S. Pat. No. 4,028,217 describes a method of separating chlorophyll from living organisms and organic solvents such as methyl alcohol, acetone, among others. The mixture is triturated and treated with dioxane, followed by a buffer phosphate solution.

Finally, document U.S. Pat. No. 6,376,698 discloses a process of removing compounds relating to chlorophyll and to gums from plant oils. This removal is carried out by using acids such as sulfuric acid and phosphoric acid.

From the description of the present invention hereinafter, one can conclude that no teaching from the prior art presents a process for preparing chlorophyll-free jambu extract by means of a selective basic hydrolysis reaction thereof, without causing the concomitant hydrolysis of spilanthol, an isobutylamide. Further, the present invention exhibits a very high efficacy relative to the percentage of the active ingredient of interest present in the jambu extract in question. In this regard, the cosmetic compositions, also objectives of the present invention, comprise high amounts of spilanthol in their composition, which favors the users of said compositions, without, however, raising the production costs, since spilanthol is obtained by an inexpensive process and from a natural source.

SUMMARY OF THE INVENTION

An objective of the present invention is to provide a process of preparing jambu extract, which comprises the following phases and steps:
  a. mixing the ground jambu plant and an alcohol;
  b. adding a strong base;
  c. heating the mixture obtained in (b) up to a temperature of about 65° C.;
  d. filtering the mixture;
  e. adding an aqueous electrolyte solution to the filtered mixture obtained in (d) and stirring;
  f. keeping the hydroalcoholic solution plus electrolyte obtained in (e) at rest for a period of 1 to 12 hours;
  g. filtering and decanting the solid residue;
  h. adding to the alcohol:water solution obtained in (g) an organic solvent soluble in spilanthol at a proportion ranging from 1:1:0.25 to 1:1:2 in terms of volume;
  i. adding a drying agent;
  j. filtering the solution and evaporating the organic solvent.

A further objective of the present invention is the use of the jambu extract obtained by the process described above, as well as a cosmetic composition comprising said jambu extract and a cosmetic product comprising said composition.

BRIEF DESCRIPTION OF THE FIGURE

FIG. 1—is a schematic representation of the complete process of preparing the jambu extract of the present invention.

DETAILED DESCRIPTION OF THE INVENTION

From the jambu extract obtained by the process of the present invention, one can prepare a cosmetic composition that provides a feeling of freshness. Since it is a quite soft cosmetic composition and has a pH of about 7.0, it is indicated for sensitive skins.

The main examples of products that may be prepared from the above-mentioned cosmetic composition are:
  body and face balm;
  postdepilatoty balsam;
  hair-removing balsam;
  lipstick or lip gloss;
  body and face gel;
  body or face moisturizer;
  body and face moisturizing milk;
  body and face moisturizing lotion;
  body or face cosmetic preparation for children;
  body and face antispot products;
  depilatory product;
  insect-repelling product;
  sun-screen or sun-block for adults and children;
  lip sun-screen or sun-block for adults and children.

The process of preparing jambu extract of the present invention has a variety of advantages over the processes known from the prior art, some of which are listed below.

The process of preparing jambu extract uses inexpensive reactants, which brings about a reduction of costs of the final products that comprise the extract obtained by this process;
  The process comprises a reduced number of steps, which are easy to carry out;
  The efficacy of the process is quite high. The spilanthol content present in the jambu extract obtained by the process of the present invention is preferably of up to 28.7% in dry mass. In addition, the final content obtained can be even higher, if one uses another sample of jambu plant having a higher initial spilanthol content than that of the preferred sample of the present invention (of about 0.16% by dry mass of plant);
  The yield of the process is also quite high, being estimated at higher than 85%;
  While carrying out the process of the present invention, a selective basic hydrolysis reaction of chlorophyll takes place. The chlorophyll, just as the spilanthol, is fat-soluble, enabling the releases of the phytol group, transforming it into chlorophyllin, which is water-soluble. Non-occurrence of hydrolysis of spilanthol, as in the process of the present invention, preserves the compound, besides keeping it fat-soluble, enabling the separation thereof from chlorophyllin, that is to say, the product of hydrolysis of chlorophyll;
  Since the whole chlorophyll and derivatives present in the natural jambu extract are removed by carrying out the process of the present invention, the cosmetic compositions comprising the final product of said process may exhibit the coloration according to the active and/or the dye added to them. In this regard, such cosmetic compositions exhibit a strong commercial and marketing appeal thanks to its visual aspect.
  The process of the present invention is indicated herein for the removal of chlorophyll from jambu extract. However, it is also effective for removing chlorophyll from other plant extracts and oils, especially for those that contain amides of cosmetic interest.

Process of Preparing Jambu Extract of the Present Invention

The process of preparing jambu extract comprises saponifying chlorophyll, transforming it into chlorophyllin and phytol. The process of the present invention comprises the following steps:
  a. mixing the ground jambu plant and an alcohol, preferably methanol;

b. adding a strong base, preferably sodium hydroxide;

c. heating the mixture obtained in (b) up to a specific temperature, preferably 65° C.;

d. keeping the mixture obtained in (b) for a specific period, preferably 90 minutes;

e. filtering the mixture;

f. adding an aqueous electrolyte solution to the filtered mixture obtained in (e), preferably 1% (w/v) aluminum sulfate in equal volume of the filtered alcoholic solution and stirring;

g. keeping the hydroalcoholic solution plus electrolyte obtained in (f) at rest for a determined period, preferably 6 hours;

h. filtering and discarding the solid residue;

i. adding to the alcohol:water solution obtained in (h) an organic solvent soluble in spilanthol, such as hexane; at the preferred ratio of 1:1:0.25 methanol:water:hexane in terms of volume;

j. repeating the process described in (i) a few more times, preferably 5 times;

k. adding a drying agent, such as anhydrous sodium sulfate to the organic solvent, preferably in the amount of 0.3 g/ml of non-polar organic solvent;

l. filtering the solution and evaporating the organic solvent.

As an alternative to sodium hydroxide, one may use other strong bases such as potassium hydroxide. Moreover, one may use options of components for hexane, as long as they are organic solvents that exhibit polarity similar to that of this compound, such as di-chloromethane, chloroform, benzene, heptane and pentane, in addition to isomers of hexane, and as long as the spilanthol is soluble therein, as is the case of hexane.

Further, the use of methanol is indicated in this phase, because, besides removing spilanthol from the jambu plant, it is little miscible with non-polar solvents, permitting the separation of spilanthol from chlorophyll. However, other alcohols may be employed, provided that they remove spilanthol from the jambu plant in the step (a).

It is interesting to use the combination of methanol and water, because, as already said before, methanol removes spilanthol and chlorophyll initially, but after the basic hydrolysis the addition of water to methanol allows the solubility of spilanthol to be lower in this mixture than in hexane, in addition to the fact that the solubility of saponified chlorophyll is higher in the methanol:water mixture than in methanol only.

The selective basic hydrolysis of chlorophyll, which just as spilanthol is fat-soluble, enables the release of the phytol group from the chlorophyll, transforming it into chlorophyllin, which is water-soluble. Non-occurrence of hydrolysis of spilanthol, as in the process of the present invention, preserves the compound, besides keeping it fat-soluble, enabling the separation thereof from chlorophyllin, that is to say, the product of hydrolysis of chlorophyll. This selective hydrolysis of the ester bond of the phytol and not of the amide bond of spilanthol depends upon the base used, upon its concentration in the reaction medium, upon the temperature and the time of reaction. The good condition of the spilanthol is guaranteed by monitoring its concentration after the hydrolysis reaction, by using the high performance liquid chromatography technique (HPLC).

The ratio of methanol and water used in step (d) must always be 1:1. However, the ratios of methanol, water and hexane used in step (g) may range from 1:1:0.25 to 1:1:2.

The addition of aluminum sulfate is necessary for removing the hydroxide that has not reacted with chlorophyll. At the same time as the hydroxide is removed by formation of aluminum hydroxide, lowering the pH to values between 6.00 and 7.00, the aluminum hydroxide is a flocculating agent, providing the precipitation of chlorophyllin and other chemical compounds, facilitating the subsequent steps of the process, rendering the purification of the spilanthol more effective.

By carrying out all the steps cited above, one obtains a jambu extract comprising essential oils, fatty acids, flavonoids and spilanthol, wherein more than 28% of the composition is of spilanthol, based on the dry mass of said extract.

The factors that should be specially controlled in this process are:

the amount of the strong base, which may range from 0.02 mol/L to 1.00 mol/L, based on the total volume of the solution obtained in step (a);

the temperature used in the hydrolysis reaction in step (b) should be between 45° C. and 75° C.;

the reaction time of step (c) should range from 60 to 90 min;

the rest time of step (d) should range from 1 to 12 h;

the ratio of the solvents methanol:water:hexane of step (i) should range from 1:1:0.25 to 1:1:2; and the amount of drying agent added in step (k) should range from 0.03 to 0.10 g/ml of the solvent to be evaporated.

Example of Process of Preparing the Jambu Extract

The example given hereinafter is a preferred variation of the process of preparing jambu extract of the present invention and should not be construed as a limitation of the invention. In this regard, one should understand that the scope of the present invention embraces other possible variations, being limited only by the contents of the set of claims, which include the possible equivalents.

The process of preparing the jambu extract comprises the following steps:

1. In a glass reactor having a capacity for 5 liters, adding 300 g of dry whole jambu plant without roots;

2. adding 3,000 ml of methanol;

3. adding 24 g of NaOH dissolved in 100 ml of water; the final concentration of NaOH should be of 0.2 mol/L;

4. raising the temperature up to the boiling point (65° C.);

5. leaving under mechanical agitation and putting to reflux for 90 min;

6. filtering the still hot material, discarding the non-extracted material (leaves, etc.);

7. measuring the volume, considering the estimated loss of 30% of the initial volume;

8. adding an equal volume of aqueous 1% (w/v) $Al_2(SO_4)_3$ solution;

9. stirring mechanically and leaving at rest in a separatory funnel for 6 hours;

10. filtering in a qualitative filter paper with the aid of Büchner funnel;

11. joining the filtrates, measuring the volume and extracting with ⅛ of the hexane volume under mechanical agitation. The ratio methanol:water:hexane will be 1:1:0.25;

12. repeating the partition with hexane for another 5 times, using the same volume of the first partition;

13. joining the hexane fractions;

14. adding anhydrous $Na_2SO_4$ at the proportion of 0.03 g/ml for removing the moisture;

15. filtering in a qualitative filter paper;

16. evaporating the hexane in a rotaevaporator until complete evaporation of the hexane.

Cosmetic Composition of the Present Invention

The cosmetic composition of the present invention comprises jambu extract as prepared by the process described before. In addition to this component, the cosmetic composition may comprises a combination of components known from the prior art.

Some examples of compounds that may be used in preparing the cosmetic composition of the present invention are:

a carrier such as water;

a thickening agent such as xanthan gum and alkyl acrylate TR-1;

a conditioning agent such as sorbitol and alga extract;

a wetting agent such as glycerin;

an emulsifying agent such as glycol stearate and glyceryl stearate;

an emollient such as Shea butter;

an antioxidant agent such as BHT;

a silicone such as cyclomethicone and dimethicone;

a preservative agent such as propylparaben and methylparaben;

among other cosmetically acceptable agents.

Examples of Cosmetic Compositions Comprising Jambu Extract Obtained by the Process of the Present Invention Like the example for the process described before, the example of a composition given hereinafter is a preferred variation of the present invention and should not be construed as a limitation of the invention. In this regard, one should understand that the scope of the present invention embraces other possible variations, being limited only by the contents of the set of claims, which include the possible equivalents.

The examples of the cosmetic composition given hereinafter contain at least one oil phase and one water phase.

The oil phase may comprise:

silicones in general;

plant oils;

butters;

waxes;

esters;

mineral oils;

emulsifiers such as polysorbates, propoxylated fatty alcohols, ethoxylated fatty alcohols, alkyl glycosides and polyglycosides, ethoxylated esters, among others.

On the other hand, the aqueous phase may contain:

thickener agents such as xanthan gum, acrylates or carbomers;

wetting agents, especially glycerin;

sensorial-property modifying agents such as biosaccharide-1 gum;

among other ingredients.

In addition, the cited preparations may contain several additives, aiming at the treatment of the skin, as for example:

vitamins;

plant extracts;

modified or non-modified peptides and amino acids;

biosaccharide gums;

hydrolyzed proteins;

caffeine and derivatives thereof;

other actives known from the prior art.

According to the use of certain types of components, with the adjustment of their concentrations and with the choice of specific actives, the compositions exemplified hereinafter may be intended for both the treatment of the face skin and for the treatment of the body skin.

Example 1

Intensive Moisturizer

| Component | Amount (g) | Amount (wt %) |
| --- | --- | --- |
| Demineralized water | 77.75 | Qsp 100 |
| Alkyl acrylate TR-1 | 0.2 | 0.002 |
| Xanthan gum | 0.2 | 0.002 |
| Alga extract and sorbitol | 0.2 | 0.002 |
| Glycerin | 10 | 0.100 |
| Dibutyl adipate | 2.0 | 0.020 |
| Glycol stearate | 2.0 | 0.020 |
| Shea butter | 0.5 | 0.005 |
| Glyceryl stearate | 0.2 | 0.002 |
| Estearet-21 | 0.7 | 0.007 |
| BHT | 0.05 | 0.0005 |
| Estearet-2 | 2.1 | 0.021 |
| Cetyl lactate | 1.0 | 0.010 |
| Iodoprinyl butylcarbamate | 0.2 | 0.002 |
| Fenoxiethanol F | 0.9 | 0.009 |
| Cyclomethicone | 1.0 | 0.01 |
| Essence | 0.75 | 0.0075 |
| Triclosan | 0.05 | 0.0005 |
| Triethanolamine | 0.1 | 0.001 |
| Jambu extract | 0.1 | 0.001 |

Example 2

Body Milk

| Component | Amount (g) | Amount (wt %) |
| --- | --- | --- |
| Demineralized water | 77.2 | Qsp 100 |
| Disodium EDDA | 0.1 | 0.001 |
| Xanthan gum | 0.2 | 0.002 |
| Carbomer | 0.4 | 0.004 |
| Glycerin | 5.0 | 0.50 |
| Methylparaben | 0.2 | 0.002 |
| Isopropyl stearate | 2.5 | 0.025 |
| Cetearet 20 | 2.0 | 0.020 |
| BHT | 0.05 | 0.0005 |
| Propylparaben | 0.1 | 0.001 |
| Propoxylated stearyl alcohol | 4.0 | 0.040 |
| Sodium hydroxide | 0.1 | 0.001 |
| Cyclomethicone | 5.0 | 0.050 |
| Dimethicone | 2.0 | 0.020 |
| 2-bromo-2-nitropopan-1,3-diol | 0.1 | 0.001 |
| Triclosan | 0.05 | 0.0005 |
| Jambu extract | 1.0 | 0.010 |

Example 3

Dynamizing Gel

| Component | Amount (g) | Amount (wt %) |
| --- | --- | --- |
| Demineralized water | 75.97 | 0.7597 |
| Butyleneglycol | 3.0 | 0.03 |
| Glycerin | 5.0 | 0.05 |
| Polyacrylamide, isoparaffin and Lanet-7 | 3.5 | 0.035 |
| Cyclomethicone and dimethiconol | 1.5 | 0.0015 |
| Essence | 0.18 | 0.0018 |
| Pantenol | 0.1 | 0.001 |

-continued

| Component | Amount (g) | Amount (wt %) |
|---|---|---|
| Cyclomethicone and dimethicone Copolymer | 6.0 | 0.06 |
| Phenoxyethanol | 1.0 | 0.01 |
| 3-iodo-2-propinylbutyl carbamate | 0.2 | 0002 |
| BHT | 0.05 | 0.0005 |
| Jambu extract | 0.5 | 0.005 |

The invention claimed is:

1. A process of preparing jambu extract, characterized by comprising the following steps:
 a. mixing the ground jambu plant and an alcohol that extracts chlorophyll and spilanthol to form a mixture;
 b. adding a hydroxide strong base to the mixture obtained in (a);
 c. heating the mixture obtained in (b) up to a temperature of about 65° C.;
 d. filtering and discarding solid residue from the mixture obtained in (c);
 e. adding an aqueous aluminum sulfate solution to the filtered mixture obtained in (d) and stirring;
 f. keeping the mixture obtained in (e) at rest for a period of 1 to 12 hours;
 g. filtering and discarding the solid residue from the mixture obtained in (f);
 h. adding to the mixture obtained in (g) an organic solvent for spilanthol selected from hexane or other organic solvent that exhibits a polarity similar to hexane at a ratio of alcohol:water:solvent of from 1:10.25 to 1:1:2 by volume;
 i. adding a drying agent to the mixture obtained in (h); and
 j. filtering the mixture obtained in (i) and evaporating the organic solvent.

2. A process according to claim 1, characterized in that the alcohol used in step (a) is methanol.

3. A process according to claim 1, characterized in that the strong base used in step (b) is selected from sodium hydroxide and potassium hydroxide.

4. A process according to claim 1, characterized in that the solvent used in step (h) is hexane.

5. The process according to claim 1, wherein the yield of spilanthol is more than 28% by dry mass of the prepared jambu extract.

6. The process according claim 1, wherein step (c) comprising selective hydrolysis of chlorophyll in the presence of spilanthol.

* * * * *